(12) United States Patent
Chen et al.

(10) Patent No.: US 9,272,010 B2
(45) Date of Patent: Mar. 1, 2016

(54) HERBAL EXTRACT AND A METHOD OF TREATING LIVER CANCER

(71) Applicant: KINGLAND REAL ESTATE CO., LTD., Taipei (TW)

(72) Inventors: Wei-Cheng Chen, Taipei (TW); Mei-Chou Lai, Taipei (TW); Shorong-Shii Liou, Taipei (TW); I-Min Liu, Taipei (TW)

(73) Assignee: KINGLAND REAL ESTATE CO., LTD., Taipei (TW)

( * ) Notice: Subject to any disclaimer, the term of this patent is extended or adjusted under 35 U.S.C. 154(b) by 0 days.

(21) Appl. No.: 14/530,045

(22) Filed: Oct. 31, 2014

(65) Prior Publication Data

US 2015/0366921 A1     Dec. 24, 2015

(30) Foreign Application Priority Data

Jun. 20, 2014   (TW) .............................. 103121455 A (51) Int. Cl.
*A61K 36/07* (2006.01)
*A61K 36/19* (2006.01)

(52) U.S. Cl.
CPC ................. *A61K 36/07* (2013.01); *A61K 36/19* (2013.01)

(58) Field of Classification Search
None
See application file for complete search history.

(56) References Cited

U.S. PATENT DOCUMENTS

| 2012/0003262 A1* | 1/2012 | Bae et al. ................ 424/195.15 |
| 2013/0129773 A1 | 5/2013 | Chiang et al. |

OTHER PUBLICATIONS

Siripong (J. Trad. Med. (2006), vol. 23, pp. 166-172).*

* cited by examiner

*Primary Examiner* — Susan Hoffman
(74) *Attorney, Agent, or Firm* — Muncy, Geissler, Olds & Lowe, P.C.

(57) ABSTRACT

The invention discloses an herbal extract of treating liver cancer, wherein a method of producing the herbal extract comprising the steps of: blending *Antrodia cinnamomea*, *Rhinacanthus nasutus* and *Phellinus linteus* and obtaining a mixture, wherein the weight percentages of *Antrodia cinnamomea*, *Rhinacanthus nasutus* and *Phellinus linteus* are 33.4 to 60%, 20 to 33.4% and 20 to 33.4% by weight of the mixture, respectively; soaking the mixture with a 95% ethanol solution with a weight-volume percentage being 50%, followed by extracting at 50 to 80° C.; and concentrating the extracted product to obtain the herbal extract. The invention also discloses a method of treating liver cancer.

3 Claims, 6 Drawing Sheets

HERBAL EXTRACT AND A METHOD OF TREATING LIVER CANCER

BACKGROUND OF THE INVENTION

1. Field of the Invention

The present invention generally relates to an herbal extract and, more particularly, to an herbal extract extracting from a mixture containing *Antrodia cinnamomea, Rhinacanthus nasutus* and *Phellinus linteus*. The present invention further relates to a method of treating liver cancer.

2. Description of the Related Art

According to Health Promotion Administration, Ministry of Health and Welfare in Taiwan, liver cancer is the second leading causes of cancer death in Taiwan and a total of 7,000 deaths are reported every year. The major reason is the prevalence of chronic hepatitis B and hepatitis C, which eventually causes cirrhosis or liver cancer.

Conventional treatment of liver cancer includes surgical resection and liver transplantation. Moreover, patients without qualification for a liver transplant have to choose an alternative treatment, such as radiofrequency ablation. However, radiofrequency ablation is a high cost treatment, has a higher possibility of causing complication, and is only suitable for small tumors (<2 cm).

*Antrodia cinnamomea*, a fungus indigenous to Taiwan, grows on decayed *Cinnamomum kanehirai*. *Antrodia cinnamomea* is rich in active ingredients such as triterpenes and superoxide dismutases and commonly used for liver protection.

*Antrodia cinnamomea* belongs to herbs with cold property and shows effect on removing free radicals and mitigating inflammation. However, a long-term application of *Antrodia cinnamomea* may excessively remove free radicals, resulting in a cold constitution with reduced immunity.

*Rhinacanthus nasutus* shows effects on relieving internal heat production and detoxication. *Phellinus linteus* contains polysaccharides as major active ingredients, which is capable of activating immunity system and improving immunity.

In light of this, it is necessary to provide an herbal extract and a method of treating liver cancer.

SUMMARY OF THE INVENTION

It is therefore the objective of this invention to provide an herbal extract as an active substance against liver cancer, inhibiting liver cancer progression in combination with the conventional method.

It is another objective of this invention to provide an herbal extract with decreased side effects, such as the cold constitution with reduced immunity, due to long-term administration of *Taiwanofungus camphorates*.

It is yet another objective of this invention to provide a method of treating liver cancer, by administering the herbal extract, preventing from proliferation of liver cancer cells and inhibiting liver cancer progression.

One embodiment of the invention discloses an herbal extract of treating liver cancer, wherein a method of producing the herbal extract comprising the steps of: blending *Antrodia cinnamomea, Rhinacanthus nasutus* and *Phellinus linteus* and obtaining a mixture, wherein the weight percentages of *Antrodia cinnamomea, Rhinacanthus nasutus* and *Phellinus linteus* are 33.4 to 60%, 20 to 33.4% and 20 to 33.4% by weight of the mixture, respectively; soaking the mixture with a 95% ethanol solution with a weight-volume percentage being 50%, followed by extracting at 50 to 80° C.; and concentrating the extracted product to obtain the herbal extract.

In a preferred form shown, the weight percentages of *Antrodia cinnamomea, Rhinacanthus nasutus* and *Phellinus linteus* are 60%, 20% and 20% by weight of the mixture, respectively.

In a preferred form shown, the extraction is performed by double boiling.

In a preferred form shown, the extraction is performed for 10 hours.

The other embodiment of the invention discloses a method of treating liver cancer, by administering the herbal extract mentioned above to a subject in need thereof to suppress proliferation of liver cancer.

In another preferred form shown, the herbal extract is orally administered to the subject in need thereof.

In another preferred form shown, the herbal extract is administered to the subject in need thereof in a dosage of 10 to 30 mg/per kilogram of body weight per day for 30 days.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

In the various figures of the drawings, the same numerals designate the same or similar parts. Furthermore, when the term "first", "second", "third", "fourth", "inner", "outer", "top", "bottom" and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

An herbal extract according to the present invention is obtained from the method comprising the steps of: blending *Antrodia cinnamomea, Rhinacanthus nasutus* and *Phellinus linteus* in an adequate ratio; extracting the mixture involving *Antrodia cinnamomea, Rhinacanthus nasutus* and *Phellinus linteus* by a 95% ethanol solution; and concentrating the extracted product to obtain the herbal extract.

In detail, the mixture contains 33.4 to 60 wt % of *Antrodia cinnamomea*, 20 to 33.4 wt % of *Rhinacanthus nasutus*, and 20 to 33.4 wt % of *Phellinus linteus*. Preferably, the mixture contains 60 wt % of *Antrodia cinnamomea*, 20 wt % of *Rhinacanthus nasutus* and 20 wt % of *Phellinus linteus*. Preferably, *Antrodia cinnamomea, Rhinacanthus nasutus* and *Phellinus linteus* are smashed into particles able to pass through a standard #30 sieve before the blending, thereby increasing efficiency of the blending and the extraction followed by.

In the embodiment, fruit bodies of *Antrodia cinnamomea* obtained from *Cinnamomum kanehirai* are used due to a higher content of triterpenoids compared with mycelia of *Antrodia cinnamomea*. Moreover, fruit bodies of *Rhinacanthus nasutus* rich in natural amino acids and trace elements are used due to effects on promoting hepatic metabolism and liver regeneration, decreasing serum glutamic-oxalocetic transaminase (GOT) and glutamate pyruvate transaminase (GPT) contents, and reducing replication of hepatitis viruses. Also, whole plants of *Phellinus linteus* with cancer-suppressing rhinacanthin can be used.

The mixture is then soaked in the 95% ethanol solution in a weight-volume percentage of 50%. That is, 1 liter of the 95% ethanol solution is used for soaking 500 grams of the mixture. The extraction is performed at 50 to 80° C. for 8 to 12 hours. Preferably, the extraction is performed by double boiling at 50° C. for 10 hours. Besides, the extraction may be performed for several times to totally dissolve the active ingredients of *Antrodia cinnamomea, Rhinacanthus nasutus* and *Phellinus linteus* in the 95% ethanol solution.

The concentrating process of the embodiment is vacuum filtrated by a No. 3 filter paper, vacuum concentrated to remove the solvent (more than half of the 95% ethanol solution used in the extraction), and followed by freeze-drying at −60° C. After the concentrating process, the herbal extract with water content smaller than 10% is obtained.

The herbal extract of the invention contains active ingredients such as triterpenes and polysaccharides. By the ratio of *Antrodia cinnamomea, Rhinacanthus nasutus* and *Phellinus linteus*, the herbal extract of the invention shows effects on preventing from cancer cell proliferation, and inhibiting liver cancer progression. Preferably, the herbal extract can be orally administered to a subject in need in a dosage of 10 to 30 mg/per kilogram of body weight of the subject in need per day for 30 days.

In order to evaluate the herbal extract of the embodiment comprises triterpenes and polysaccharides, and to further verify the herbal extract of the invention poses ability of inhibition liver cancer proliferation, trials (A) to (C) are performed as following.

Trial (A): Contents of Active Ingredients

Referring to TABLE 1, 500 grams of the mixtures (with different amount of *Antrodia cinnamomea, Rhinacanthus nasutus* and *Phellinus linteus*) are used in trial (A). The mixtures blend with 1 liter of the 95% ethanol solution and the extraction is performed by double boiling at 50° C. for 8 hours. The resulted product are further filtrated by a No. 3 filter paper, vacuum concentrated to remove the 95% ethanol solution (more than half of 95% ethanol used in the extraction), followed by freeze-drying at −60° C. to obtain the herbal extracts of groups A1 to A3. Following trials with the herbal extracts are carried on. The yield (%) shown in TABLE 1 is calculated as the following formula:

$$\text{Yield}(\%) = (\text{obtained amounts})/500 \times 100\%$$

TABLE 1

| | Amounts of mixtures (g) | | | |
|---|---|---|---|---|
| Groups | Antrodia cinnamomea | Rhinacanthus nasutus | Phellinus linteus | Herbal extract Yield (%) |
| A1 | 167 | 167 | 167 | 10.1 ± 1.6 |
| A2 | 250 | 125 | 125 | 11.4 ± 1.4 |
| A3 | 300 | 100 | 100 | 12.3 ± 1.5 |

Moreover, 0.2 grams of the herbal extracts shown in TABLE 1 are ultrasonic vibrated with 5 mL of methanol for 15 minutes, followed by centrifugation at 3,000 rpm for 10 minutes. 5 mL of supernatants are collected into new tubes, followed by heating with 100° C. water bath to dry.

For analyzing triterpenes, Purospher STAR (purchased from Merck) RP-18e (5 μm) 250 mm×4 mm column is used. A mobile phase is acetonitrile and 0.085% phosphoric acid mixed in a volumetric ratio of 47:53. A flow rate of the mobile phase is 1 mL/min. Absorbance of 254 nm is detected, and the area under the curve is analyzed to verify the amount of triterpenes.

Figure 1A:
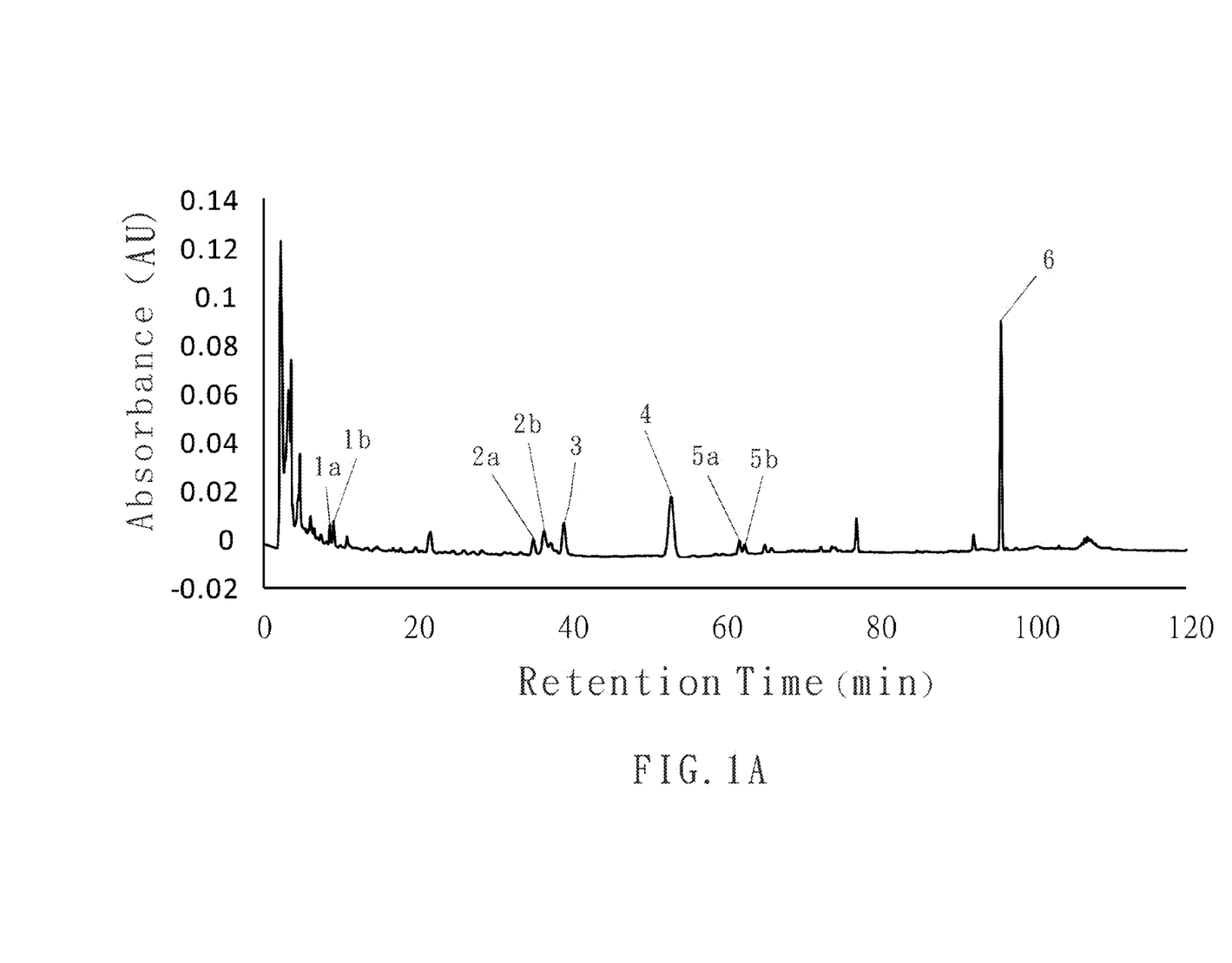
FIG. 1A depicts content of triterpenoids of group A1 using HPLC analysis.
Figure 1B:
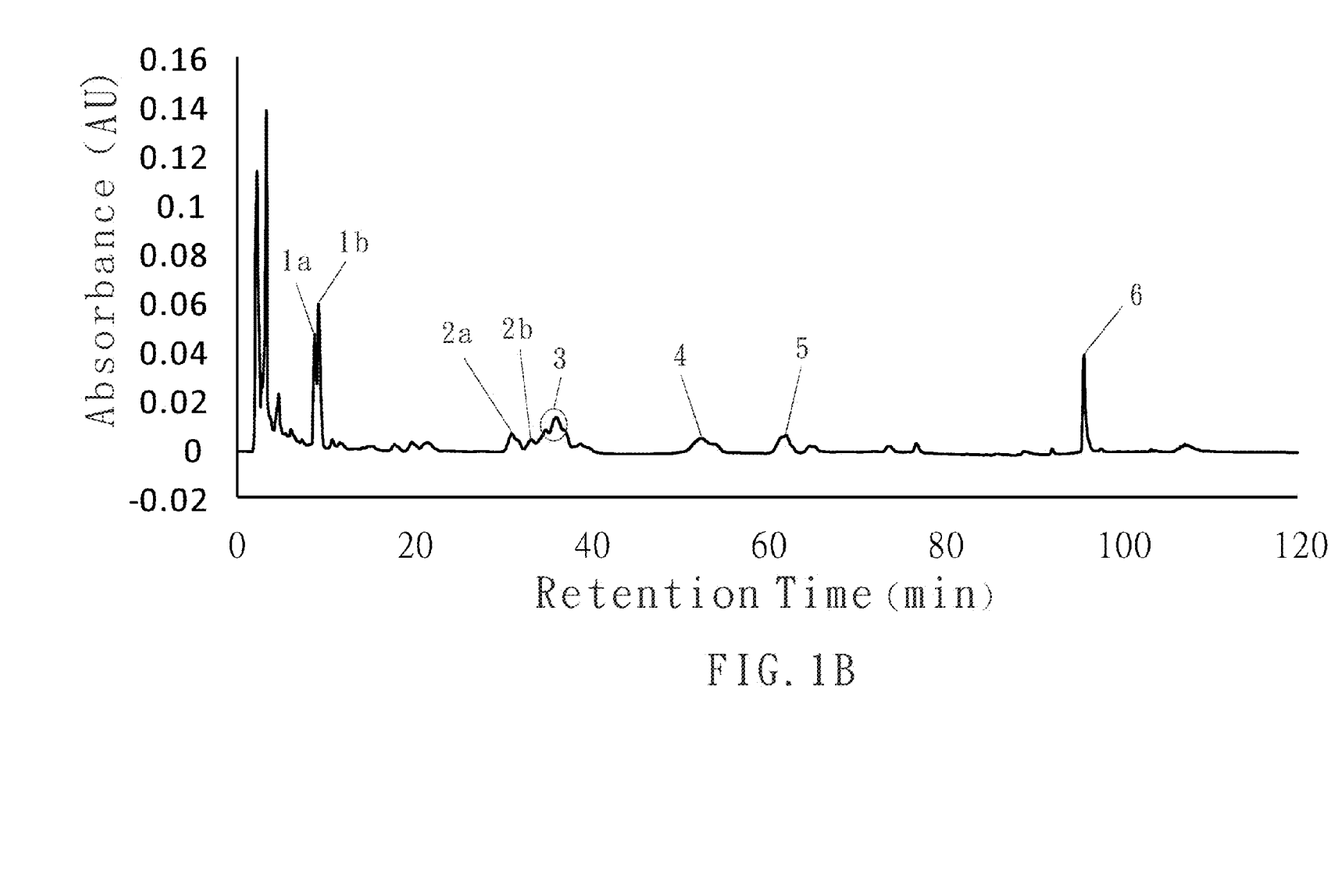
FIG. 1B depicts content of triterpenoids of group A2 using HPLC analysis.
Figure 1C:
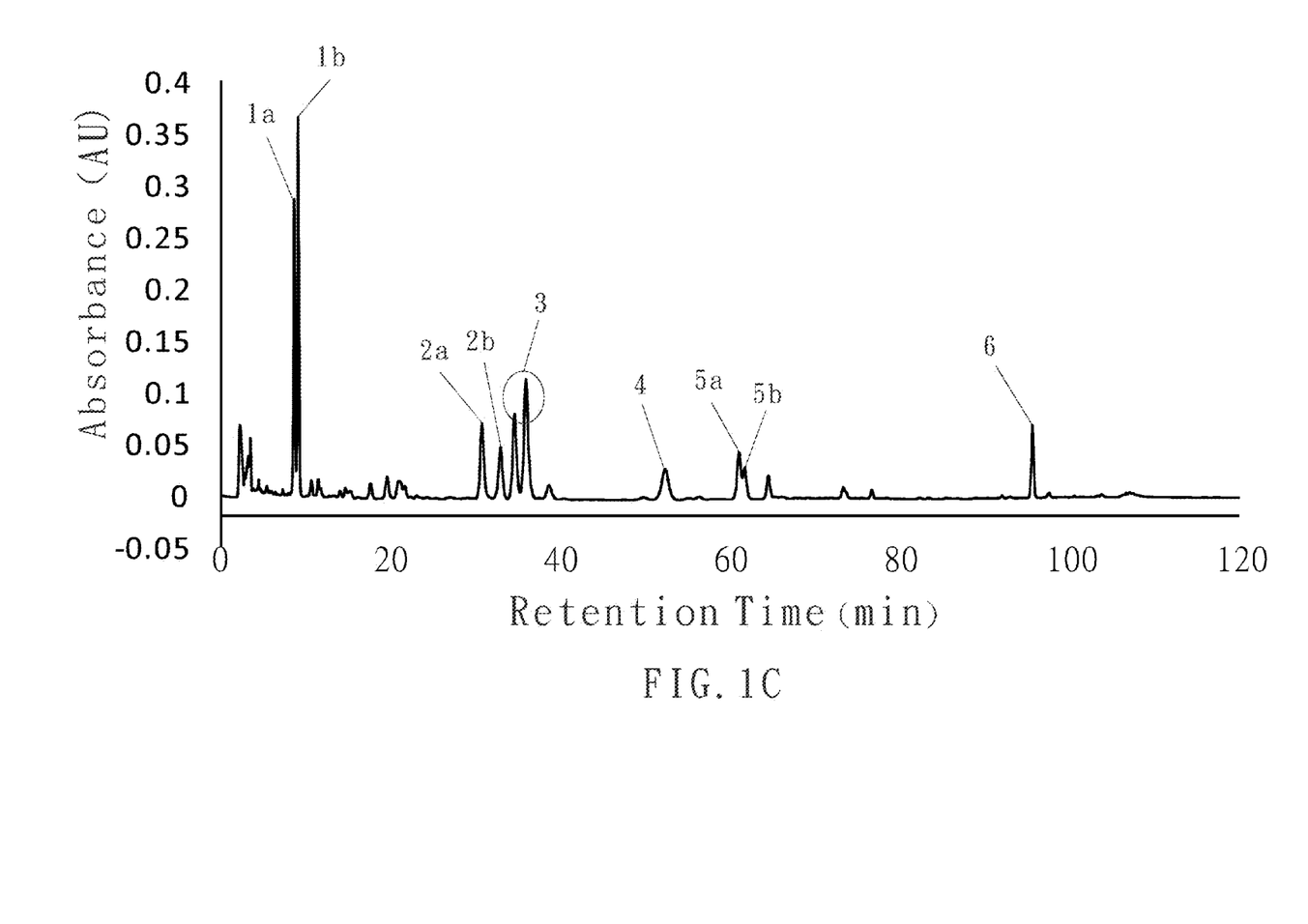
FIG. 1C depicts content of triterpenoids of group A3 using HPLC analysis.

Furthermore, TABLE 2 and FIGS. 1A to 1C show contents of several reference compounds of triterpenoids, such as antcin K, antcin C, zhankuic C, dehydrosulphurenic acid, zhankuic acid A and dehydroeburicoic acid. As a result, group A3 shown in FIG. 1C contains a highest content of antcin K, antcin C, zhankuic C and zhankuic acid A.

TABLE 2

| Active ingredients | Antcin K | | Antcin C | | Zhankuic acid C | |
|---|---|---|---|---|---|---|
| Peak | 1a | 1b | 2a | 2b | 3a | 3b |
| Retention time (min)/ Ratios of Peak Area (%) | A1 8.396/ 0.834667 | 9.136/ 1.118667 | 31.426/ 0.075333 | 33.507/ 0.066000 | 35.139/ 1.417667 | 36.556/ 2.091667 |
| | A2 8.547/ 8.232333 | 9.002/ 12.51933 | 31.193/ 2.281667 | 33.367/ 0.501500 | 34.950/ 0.650000 | 36.200/ 1.503500 |
| | A3 8.700/ 9.998000 | 9.180/ 14.10167 | 30.935/ 6.325333 | 33.111/ 4.515667 | 34.824/ 7.369333 | 36.202/ 11.56033 |

| Active ingredients | Dehydrosulphurenic acid | Zhankuic acid C | | Dehydroeburicoic acid | |
|---|---|---|---|---|---|
| Peak | 4 | 5a | 5b | 6 | Total* |
| Retention time (min)/ | A1 53.098/ 8.836667 | 61.916/ 0.944000 | 62.602/ 0.549000 | 95.935/ 12.09467 | —/ 28.02633 |
| | A2 52.433/ | 61.929/ | 64.987/ | 95.900/ | —/ |

TABLE 2-continued

| | | | | | |
|---|---|---|---|---|---|
| Ratios of | 1.764000 | 1.582333 | 0.540667 | 8.029333 | 37.60467 |
| Peak Area A3 | 52.807/ | 61.053/ | 61.700/ | 95.311/ | —/ |
| (%) | 4.692000 | 4.086333 | 2.415000 | 3.711333 | 68.77500 |

*Total contents is calculated as the sum of several reference compounds.

Finally, for analyzing polysaccharides, a standard curve is prepared with different concentrations of galactose. The herbal extract (1 mL) in TABLE 1 mixes with phenol solution (1 mL, 5%), and then subjected to a direct stream of concentrated sulfuric acid (5 mL). After cooling for 30 minutes, absorbance of 490 nm is measured. As shown in TABLE 3, concentrations of polysaccharides are calculated according to the standard curve.

TABLE 3

| Groups | Contents of polysaccharides (ppm) |
|---|---|
| A1 | 32.15 ± 1.28 |
| A2 | 33.41 ± 1.26 |
| A3 | 34.92 ± 1.18 |

With reference to TABLE 3, group A3 has a highest content of 34.92±1.18 ppm, while group A1 has a lowest content of 32.15±1.28 ppm.

Accordingly, the herbal extract of the embodiment is rich in triterpenes and polysaccharides, thereby poses effect on inhibiting liver cancer proliferation.

Trial (B): In Vitro Pharmacological Study

HepG2 (human liver cancer cell line, BCRC 60025) purchased from the Food Industry Research and Development Institute in Taiwan is used in trial (B). The HepG2 cells are cultured in DMEM medium (Dulbecco's Modified Eagle Medium) containing 10% FBS (purchased from Biological Industries, Kibbutz beit haemek), 2 mmol/L $_L$-glutamine (purchased from HyClone, USA), 1x nonessential amino acids (purchased from HyClone, USA), 100 μg/mL streptomycin and 100 U/mL penicillin (purchased from HyClone, USA). The HepG2 cells are incubated in an incubator with temperature of 37° C., $CO_2$ concentration of 5% and humidity of 95%. Medium used for culturing the HepG2 cells is renewed once in two days.

While subculturing, the HepG2 cells are centrifuged at 1,000 rpm for 5 minutes to remove supernatants, followed by mixing with fresh medium. The HepG2 cells preferably have a concentration of $1\times10^5$ to $1\times10^6$ cells/mL in 10 cm culturing dishes.

The culturing dishes 80 to 90% of bottom areas covered by the HepG2 cells are used in trial (B). Discolored medium is removed, 8 mL of PBS solution is used to wash the HepG2 cells and Trypsin/EDTA is added into the culturing dishes for 1 to 3 minutes. After the HepG2 cells dissociate with walls of the culturing dishes by slightly vortexing, the HepG2 cells are resuspended with prewarmed medium. The HepG2 cells are collected into centrifuge tubes, followed by centrifugation at 1,500 rpm for 10 minutes. Supernatants are removed and the HepG2 cells are resuspended in medium containing FBS. 20 μL of the HepG2 cells are collected, and 20 μL of trypan blue is added to the HepG2 cells for staining. The stained HepG2 cells are collected in cell counters, and numbers of the stained HepG2 cells are counted under microscope. Only the HepG2 cells with viability over 85% are suitable for the following experiments.

Concentrations of the HepG2 cells are adjusted to $1\times10^5$ cells/mL by medium containing FBS. 100 μL of the HepG2 cells with a concentration of $1\times10^4$ cells per are inoculated in a 96-well plate. The inoculated HepG2 cells are overnight cultured in an incubator with temperature of 37° C. and $CO_2$ concentration of 5%.

After culturing for 24 hours, 100 μL of the herbal extracts shown in TABLE 4 (in a concentration being 1, 0.5, 0.25 or 0.125 mg/mL) are added into each well of the 96-well plate. The HepG2 cells treated with DMEM is used as the negative control (group B0). The HepG2 cells are overnight cultured in an incubator with temperature being 37° C. and $CO_2$ concentration being 5%.

TABLE 4

| | | Survival Rate (%) | | | |
|---|---|---|---|---|---|
| Groups | Treatment | 1 mg/mL | 0.5 mg/mL | 0.25 mg/mL | 0.125 mg/mL |
| B0 | DMSO | 100.00 ± 0.10 | 100.00 ± 0.08 | 100.00 ± 0.12 | 100.0 ± 0.15 |
| B1 | Herbal extract (group A1) | 70.58 ± 1.06 | 80.42 ± 1.19 | 90.53 ± 1.23 | 95.37 ± 1.03 |
| B2 | Herbal extract (group A2) | 61.70 ± 1.09 | 70.29 ± 1.19 | 80.52 ± 1.21 | 90.21 ± 1.13 |
| B3 | Herbal extract (group A3) | 58.13 ± 1.16 | 65.38 ± 1.20 | 72.41 ± 1.17 | 84.63 ± 1.18 |

After culturing for 24 hours, medium is removed, and the HepG2 cells are washed by a PBS solution. 100 μL of CCK-8 containing-fresh medium is added into each well of the 96-well plate. The HepG2 cells react with CCK-8 for 2 hours in the incubator (37° C., 5% $CO_2$), followed by vortexing for 5 minutes. Absorbance of 450 nm of the tumor cells in each well is detected.

Survival rate of the HepG2 cells treated with the herbal extracts shown in TABLE 4, while the survival rate is computed as followed:

Survival rate(%)=(Absorbance of a testing set/Absorbance of a control set)×100%

Referring to TABLE 4, HepG2 cells treated with the herbal extract of group A3 in a concentration being 1 mg/mL has a survival rate of 58.13±1.16%, which is obviously lower than HepG2 cells treated with the herbal extract of A1 and A2 in the same concentration. That is, the herbal extract of group A3 according to preferred teachings of the present invention poses a better effect on inhibiting liver cancer cell proliferation.

Referring to TABLE 4, the herbal extract according to preferred teachings of the present invention poses a better effect on inhibiting liver cancer proliferation. Besides, since the herbal extract of group A3 shows the best effect, the following trial is performed using the herbal extract of group A3.

Trial (C): In Vivo Pharmacological Study

Specific-pathogen free C57BL/6 male mice (8 week-old, weight 20-25 g) purchased from The National Laboratory Animal Center (NLAC) are used in trial (C). The mice are housed in an animal room in the Experimental Animal Center of Tajen University with constant temperature of 25±1° C. where is kept on a 12-hours light and 12-hours dark cycle. The mice are housed and kept on free diet and water, which provided by the animal center of the Experimental Animal Center of Tajen University.

The HEPA 1-6 cells (mouse liver cancer cells, BCRC 60051) purchased from the Food Industry Research and Development Institute in Taiwan is used in trial (C). The HEPA 1-6 cells are cultured in DMEM medium containing 10% FBS, 2 mmol/L $_L$-glutamine, 1x nonessential amino acids, 100 μg/mL streptomycin and 100 U/mL penicillin. The HEPA 1-6 cells are incubated in an incubator with temperature of 37° C., $CO_2$ concentration of 5% and humidity of 95%. Medium used for culturing the HEPA 1-6 cells is renewed once in two days.

The HEPA 1-6 cells are diluted to a concentration of $5 \times 10^6$ cells/mL by a saline solution. The diluted HEPA 1-6 cells are inoculated to the mice via subcutaneous injection in buttock.

The herbal extract of group A3 is orally administrated to the mice in a dosage of 10, 20, 30 mg per kilograms of the mice per day for 30 days, respectively (group C1, C2 and C3). Group C0 is a control set without the herbal extract (orally fed with RO water). Tumor burden is monitored once a week.

With respect to TABLE 5, the mice are sacrificed, followed by weighting the tumor burden, liver and spleen. The liver cancer-suppressing rate is calculated. All data recorded in TABLE 5 are presented in a form of mean±S.E.M. Symbol "*" indicates $p<0.05$, compared with group C0.

groups C0 to C3. That is, the herbal extract of the invention poses effect on liver protection.

Figure 3A:
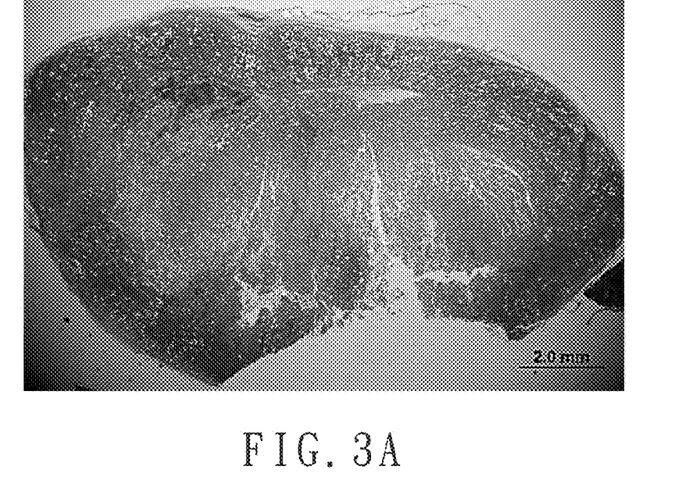
FIG. 3A depicts an H&E staining of group C0.
Figure 3B:
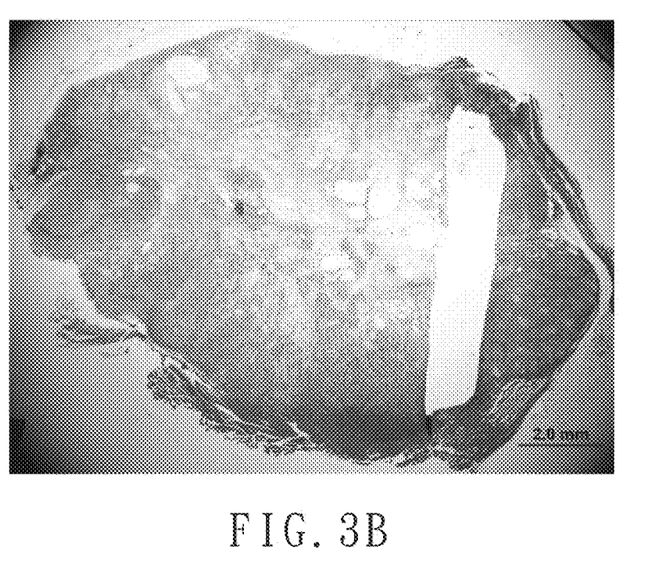
FIG. 3B depicts an H&E staining of group C1.
Figure 3C:
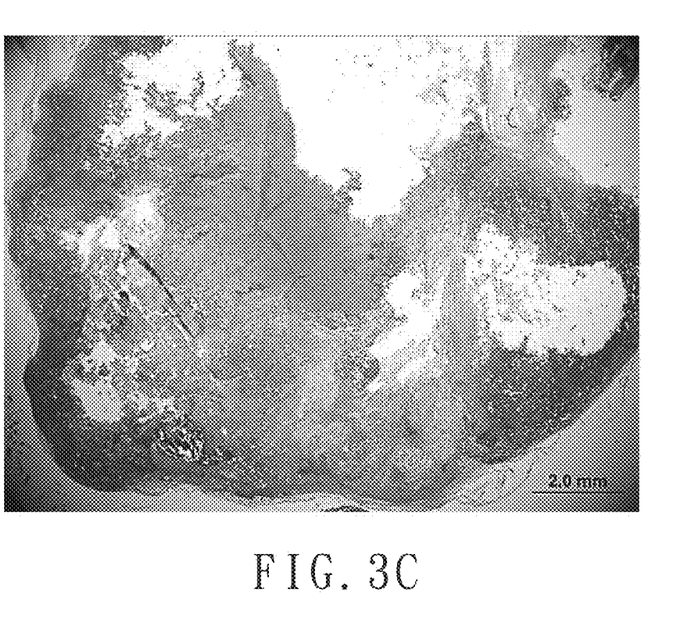
FIG. 3C depicts an H&E staining of group C2.
Figure 3D:
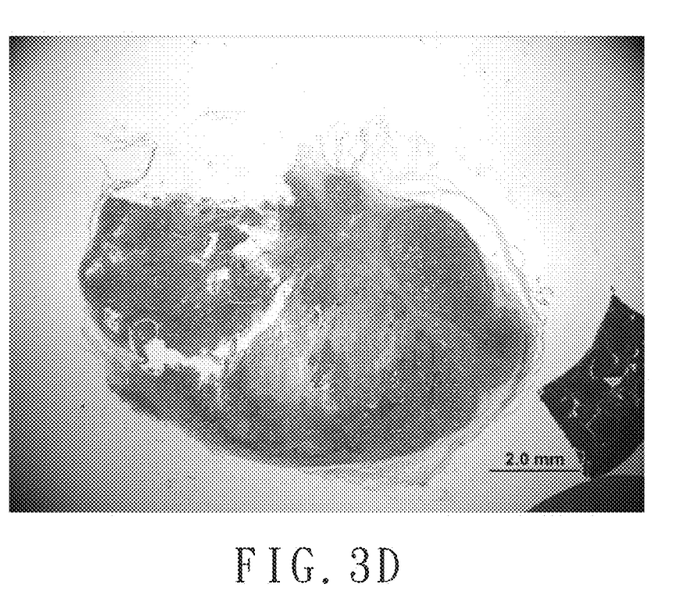
FIG. 3D depicts an H&E staining of group C3.

Furthermore, as shown in FIG. 3A, H&E staining shows the cancer cells repress muscles, leading the infiltration of adipocytes. Groups C1 to C3 shown in FIGS. 3B to 3D show local to widespread necrosis in and around the cancer, leading part of the cancer cells.

Accordingly, the herbal extract of the invention rich in several active ingredients such as triterpenes and polysaccharides can be broadly applied to different liver cancer patients in combination with the conventional treatment, thereby effectively decreasing tumor burden and inhibiting liver cancer progression.

Moreover, with abundant polysaccharides as the active ingredients, a long-term application of the herbal extract of the invention will not result in the cold constitution with reduced immunity, which is a side effect of the long-term application of *Antrodia cinnamomea*.

Besides, by administering the herbal extract of the invention with abundant active ingredients provided from *Antrodia cinnamomea*, *Rhinacanthus nasutus* and *Phellinus linteus*, the method of treating liver cancer can effectively prevent from cancer cell proliferation, accelerating necrosis of the tumor tissue, thereby inhibiting liver cancer progression.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method of treating liver cancer, comprising:
administering an herbal extract to a subject in need thereof in a dosage of 10 to 30 mg/per kilogram of body weight per day for 30 days to suppress proliferation of liver cancer,
wherein the herbal extract is produced by a method comprising the steps of:
blending *Antrodia cinnamomea*, *Rhinacanthus nasutus* and *Phellinus linteus* and obtaining a mixture consisting of 60 wt % of *Antrodia cinnamomea*, 20 wt % of *Rhinacanthus nasutus* and 20 wt % of *Phellinus linteus*;

TABLE 5

| Groups | Weight (g) | Liver (mg) | Spleen (mg) | Tumor burden (mm³) | Cancer-suppressing rate (%) | GOT (U/L) | GPT (U/L) | BUN (mg/dL) | Creatinine (mg/dL) |
|---|---|---|---|---|---|---|---|---|---|
| C0 | 25.1 ± 1.2 | 137.1 ± 0.8 | 75.2 ± 3.2 | 1512.23 ± 2.77 | — | 171.2 ± 3.2 | 10.4 ± 1.3 | 57.9 ± 5.3 | 0.65 ± 0.13 |
| C1 | 24.9 ± 1.3 | 136.7 ± 0.4 | 79.8 ± 2.9 | 1089.21 ± 1.91* | 27.97 ± 2.81 | 164.5 ± 2.6* | 9.2 ± 0.8* | 54.3 ± 4.1 | 0.63 ± 0.10 |
| C2 | 25.2 ± 1.8 | 139.2 ± 0.3 | 79.6 ± 2.4 | 932.41 ± 1.89* | 38.34 ± 2.92 | 159.5 ± 2.3* | 8.4 ± 0.5* | 52.5 ± 4.3 | 0.62 ± 0.11 |
| C3 | 25.2 ± 1.5 | 138.6 ± 0.2 | 78.1 ± 2.6 | 432.48 ± 1.78* | 71.40 ± 3.27 | 153.8 ± 2.5* | 8.3 ± 0.4* | 51.7 ± 3.2 | 0.62 ± 0.12 |

Figure 2:
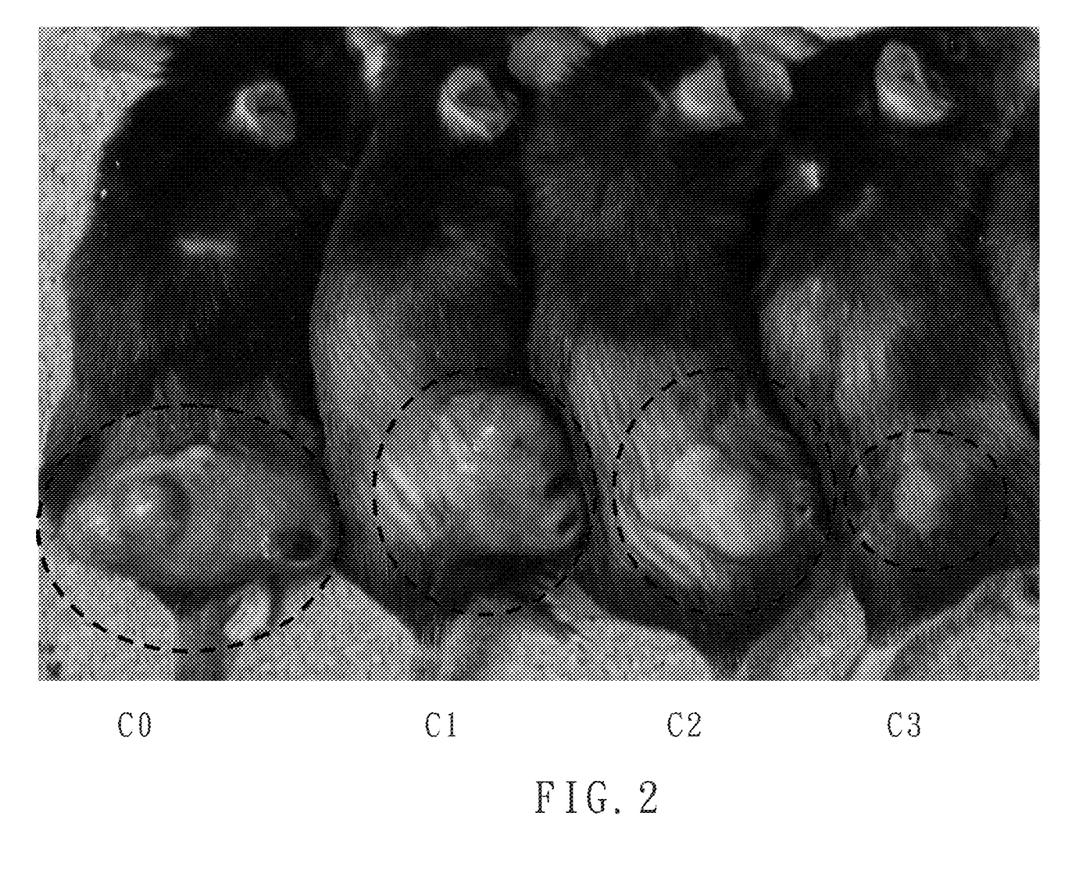
FIG. 2 depicts a photo showing appearance of tumor of groups C0 to C3.

With reference to FIG. 2, the herbal extract of the invention can effectively decrease tumor burden, compared with group C0. Furthermore, referring to TABLE 5, as the amount of the herbal extract increases, the effect on inhibiting cancer cell proliferation improves. As shown in TABLE 5, group C3 has a cancer-suppressing rate of 71.40±3.27% in a dosage of 30 mg/kg/day, obviously higher than groups C1 and C2. Moreover, the administration of the herbal extract of the invention in different dosage shows no different on body weight, liver weight and spleen weight. That is, the herbal extract of the invention will not damage non-tumor tissues.

Moreover, with reference to TABLE 5, liver function index such as GOT and GPT decreases as the administration of the herbal extract of the invention, while kidney function index such as BUN and creatinine shows no difference between soaking the mixture with a 95% ethanol solution with a weight-volume percentage being 50%, followed by extracting at 50 to 80° C.; and
concentrating the extracted product to obtain the herbal extract.

2. The method of treating liver cancer as claimed in claim 1, wherein the herbal extract is orally administered to the subject in need thereof.

3. The method of treating liver cancer as claimed in claim 1, wherein the *Antrodia cinnamomea* and *Rhinacanthus nasutus* used in the production method of the herbal extract comprise the fruiting bodies of the respective fungus.

* * * * *